United States Patent [19]

Katsumata et al.

[11] Patent Number: 5,374,542
[45] Date of Patent: Dec. 20, 1994

[54] PROCESS FOR PRODUCING 4-HYDROXY-L-PROLINE

[75] Inventors: Ryoichi Katsumata, Machida, Japan; Haruhiko Yokoi, Ottawa, Canada

[73] Assignee: Kyowa Hakko Kogyo Co., Ltd., Tokyo, Japan

[21] Appl. No.: 39,482
[22] PCT Filed: Aug. 26, 1991
[86] PCT No.: PCT/JP91/01127
§ 371 Date: Apr. 26, 1993
§ 102(e) Date: Apr. 26, 1993
[87] PCT Pub. No.: WO93/04181
PCT Pub. Date: Mar. 4, 1993

[51] Int. Cl.$^5$ .................. C12P 13/24; C12N 15/09; C12N 15/70
[52] U.S. Cl. ................ 435/107; 435/172.3; 435/252.33; 435/320.1
[58] Field of Search ............... 435/107, 252.3, 252.33, 435/320.1

[56] References Cited

U.S. PATENT DOCUMENTS

| | | | |
|---|---|---|---|
| 3,905,867 | 9/1975 | Kurimura et al. | 435/115 |
| 4,421,853 | 12/1983 | Updike et al. | 435/116 |
| 4,463,094 | 7/1984 | Chibata et al. | 435/115 |
| 4,594,323 | 6/1986 | Csonka et al. | 435/107 |
| 4,681,852 | 7/1987 | Tribe | 435/108 |
| 4,707,449 | 11/1987 | Shay | 435/255 |
| 5,017,482 | 5/1992 | Katsumata et al. | 435/1114 |
| 5,087,566 | 2/1992 | Takano et al. | 435/115 |

FOREIGN PATENT DOCUMENTS 0069697 1/1983 European Pat. Off. .
63119688 5/1993 Japan .

OTHER PUBLICATIONS

Garcia, J. L., et al., 1985, Microbiologia, 1(1):43–51.
Csonka, L. N., et al., 1988, Gene, 64(2):199–205.
Dandekar, A. M., et al., 1988, Journal of Bacteriology, 170(12):5943–5945.
Jakowec, M. W., et al., 1985, Applied and Environmental Microbiology, 50(2):441–446.
Smith, L. T., 1985, Journal of Bacteriology, 164(3):1088–1093.
Smith, C. J., et al., 1984, Journal of Bacteriology, 157(2):545–551.
Eguchi, L., et al, 1974, Bulletin of the Chemical Society of Japan 47(7):1704–1708.
Ramaswamy, S. G., et al., 1977, Journal of Organic Chemistry 42(21):3440–3442.

*Primary Examiner*—Robert A. Wax
*Assistant Examiner*—William W. Moore
*Attorney, Agent, or Firm*—Antonelli, Terry, Stout & Kraus

[57] ABSTRACT

Disclosed are a process for producing 4-hydroxy-L-proline by the conversion of 4-hydroxy-2-oxoglutaric acid in an aqueous medium in the presence of an amino group donor and an enzyme source belonging to the genus Escherichia and capable of converting 4-hydroxy-2-oxoglutaric acid into 4-hydroxy-L-proline; and a microorganism which belongs to the genus Escherichia, holds a recombinant DNA incorporating a gene coding for γ-glutamylkinase released from the feedback inhibition caused by L-proline, and contains the above enzyme source.

3 Claims, 1 Drawing Sheet

PROCESS FOR PRODUCING 4-HYDROXY-L-PROLINE

FIELD OF THE INVENTION

The present invention relates to a process for producing 4-hydroxy-L-proline by use of a microorganism capable of biosynthesizing trans-4-hydroxy-L-proline and/or cis-4-hydroxy-L-proline (hereinafter referred to as 4-hydroxy-L-proline) from D- or L-4-hydroxy-2-oxoglutaric acid (hereinafter referred to as 4-hydroxy-2-oxoglutaric acid). 4-Hydroxy-L-proline is an amino acid which is useful as an intermediate for the synthesis of pharmaceuticals, etc.

1. Background of the Invention

As the hitherto known methods for the production of 4-hydroxy-L-proline, mention may be made of a method comprising hydrolyzing collagen and recovering, from the hydrolyzed collagen-constituting amino acids, trans-4-hydroxy-L-proline; a method for synthesizing trans-4-hydroxy-L-proline from D-glutamic acid (Bulletin of the Chemical Society of Japan, 47., 1704, 1974); and a method for synthesizing trans-4-hydroxy-L-proline from glyoxal and oxaloacetic acid (Journal of Organic Chemistry, 42, 3440, 1977) are known.

The prior art methods are not satisfactory for the industrial production because of (1) high cost of raw materials, (2) many reaction steps involved and (3) problems in the recovering and purifying steps. Thus, an improved method is desired for the industrially inexpensive production of 4-hydroxy-L-proline.

2. Disclosure of the Invention

According to the present invention, 4-hydroxy-L-proline is efficiently produced by converting 4-hydroxy-2-oxoglutaric acid into 4-hydroxy-L-proline in an aqueous solution in the presence of an amino group donor and an enzyme source capable of converting 4-hydroxy-2-oxoglutaric acid into 4-hydroxy-L-proline.

Specifically, the conversion reaction of 4-hydroxy2-oxoglutaric acid into 4-hydroxy-L-proline is carried out by bringing the above-mentioned enzyme source into contact with 4-hydroxy-2-oxoglutaric acid and an amino group donor in an aqueous solution having a pH suitable for the enzyme reaction, such as a buffer and a physiological saline.

As the enzyme source to be used in the present invention, either of a purified enzyme preparation or a crude enzyme preparation may be used. Preferably, a microorganism having an enzymatic activity of converting 4-hydroxy-2oxoglutaric acid into 4-hydroxy-L-proline may be used. More specifically, the microorganism having such an activity may be used in a form of a culture, cells or processed cells.

When a microorganism is used as the enzyme source, 4-hydroxy-2-oxoglutaric acid is brought into contact with the culture obtained by culturing the microorganism, during the culturing, in order to form 4-hydroxy-L-proline in the culture.

Any microorganism can be used in the present invention so long as it has an enzymatic activity to convert 4-hydroxy-2-glutaric acid into 4-hydroxy-L-proline. As the microorganism having such enzyme activity, mention may be made of those belonging to the genus Escherichia. As the practical strain, Escherichia coli ATCC33625 is mentioned.

Mutants and genetically engineered transformants in which enzyme activity for L-proline biosynthesis has been intensified, by a recombinant DNA technology and conventional mutagenesis, etc. are preferably used. For example, a microorganism possessing γ-glutamylkinase activity of which feedback inhibition by L-proline has been released, is mentioned.

The genetically engineered transformants with the intensified enzyme activity include, for example, Escherichia coli K83. The strain carries a recombinant DNA comprising a proB gene derived from Escherichia coli MM294 strain which gene codes for γ-glutamylkinase, of which feedback inhibition caused by L-proline has been released. Such recombinant DNA-carrying strains may be produced by the method of Deutche, et al. (Nucleic Acid Research, 12, 6337, 1984) or by the methods described in the Examples in the present specification.

Escherichia coli K83 has been deposited with the Fermentation Research Agency, Industrial Science and Technology in Japan as of March 15, 1990, in terms of the Budapest Treaty, under FERM BP-2807.

The microorganism as used in the present invention may be cultured in either of a synthetic medium or a natural medium so long as it contains an appropriate amount of a carbon source, nitrogen source and inorganic substance, etc.

As the carbon source, mention may be made of a saccharide such as glucose, fructose, sucrose, maltose, lactose, starch, starch hydrolyzate, molasses, cellulose hydrolyzate, etc., an organic acid such as acetic acid, lactic acid, etc., or an alcohol such as ethanol, etc.

As the nitrogen source, mention may be made of ammonia, an ammonium salt such as ammonium sulfate, ammonium chloride, ammonium acetate, etc., or a nitrogen-containing organic compound such as urea, nitrate, peptone, meat extract, yeast extract, corn steep liquor, etc.

As the inorganic acid, mention may be made of potassium phosphate, ammonium sulfate, ammonium chloride, sodium chloride, magnesium sulfate, ferrous sulfate, manganese sulfate, etc.

Additionally, trace elements, for example metal salts such as calcium salt, zinc salt, boron salt, copper salt, cobalt salt, molybdenum salt, etc. or nutrients such as vitamins, amino acids, nucleic acids, etc. may be added to the medium to promote the growth of the microorganism. If these ingredients are included in the other supplied ingredients, there is no need to add these ingredients.

The culturing is carried out at a temperature of 20° to 40° C. and a pH value around neutrality. The culture may be used as an enzyme source as such, but usually the culture is subjected to filtration, centrifugation and the like to harvest the cells. The cells may be used as they are, but usually, processed cells which are prepared by subjecting the intact cells to ultrasonication, crushing and treatment with a surfactant, may be used.

When the microorganism has the enzymatic activity to produce 4-hydroxy-2-oxoglutaric acid from a precursor thereof, the precursor, instead of 4-hydroxy-2-oxoglutaric acid, may be supplied in the culture or the aqueous solution.

The precursor includes, for example, pyruvic acid or glyoxylic acid, which are substrates for D-4-hydroxy-2oxoglutaric acid aldolase.

The amino group donor includes, for example, amino acids such as aspartic acid, asparagine, etc., ammonium salts, urea, etc.

For the reaction of converting 4-hydroxy-L-proline from 4-hydroxy-2-oxoglutaric acid, 1–200 g/l 4-hydroxy-2-oxoglutaric acid or a precursor thereof, and a 0.1–50 g/l amino group donor are supplied in the aqueous solution or the culture.

When the microorganism is used as the enzyme source, then aspartic acid or asparagine, or a precursor thereof, may be supplied in the culture or the aqueous solution in order to produce 4-hydroxy-L-proline in higher yield. The precursor, for example, include fumaric acid and ammonia, which are substrates of aspartase, which is an enzyme involved in the production of aspartic acid or asparagine.

The produced and accumulated 4-hydroxy-L-proline may be recovered by any conventional method as applied for recovering an amino acid from a culture or aqueous solution. For example, 4-hydroxy-L-proline is isolated by subjecting a cell-free supernatant obtained by centrifugal separation, to ion-exchange resin film treatment.

PREFERRED EMBODIMENT OF THE INVENTION

EXAMPLE 1

Figure 1:
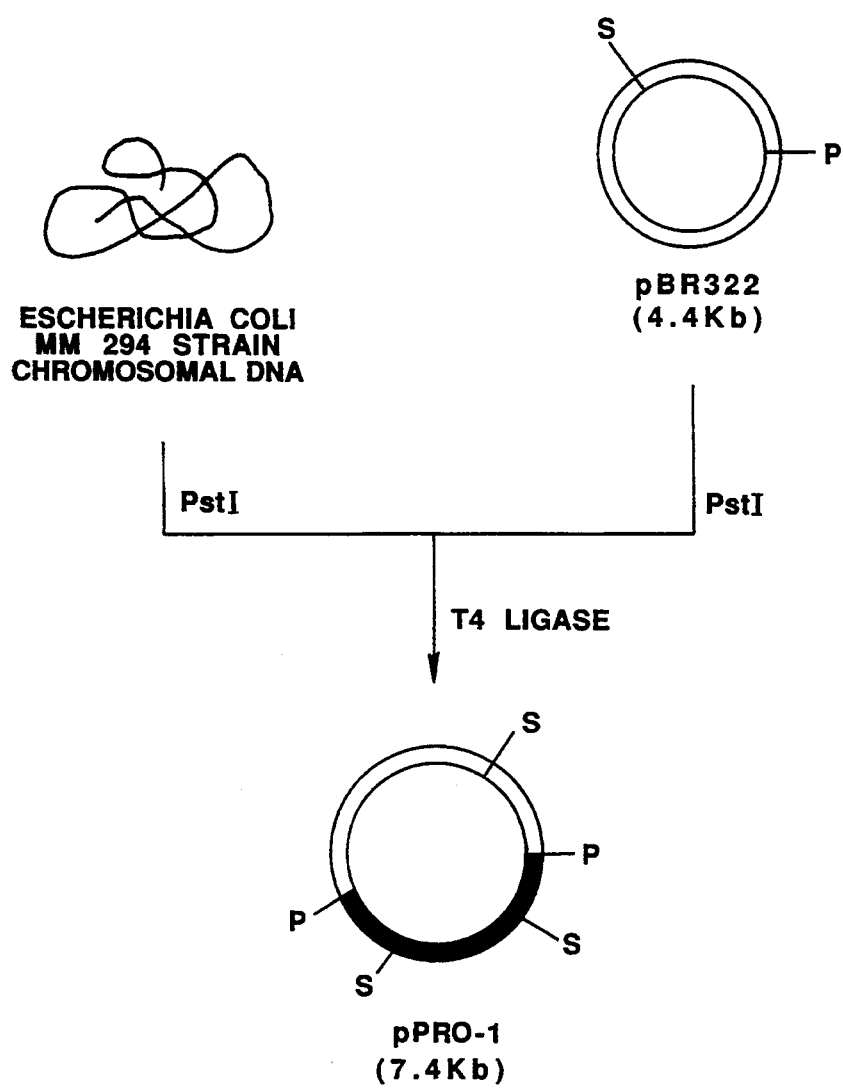
FIG. 1 is a cleavage map of the restriction enzymes PstI and SalI of plasmid pPRO-1, and the construction process for plasmid pPRO-1. In the drawing, P stands for PstI, and S stands for SalI. The size of the plasmid is expressed in kilobases (kb). The bold line of pPRO-1 indicates the DNA fragment including the ProAB gene cloned from the chromosomal DNA of MM294 strain.

1) Cloning of the proAB gene of *Escherichia coli*

The chromosomal DNA including the proAB gene of *Escherichia coli* K12 strain was isolated from *Escherichia coli* MM294 (ATCC33625) which is derived from *Escherichia coli* K12 strain, according to the method described in Biochimica et Biophysica Acta, 72, 619, 1963. As the vector, pBR322 containing the ampicillin- and tetracycline- resistant genes (commercially available from Takara Shuzo Co.) was used. To 100 μl of a reaction solution (pH 7.5) comprising 10 mM Tris, 50 mM NaCl and 7 mM MgCl$_2$ for restriction enzyme PstI and containing 1 μg of pBR322 plasmid DNA and 3 μg of MM294 chromosomal DNA, was added 16 units of PstI (product of Takara Shuzo Co.), and the mixture was allowed to stand at 37° C. for 60 minutes. The reaction was stopped by heating the mixture at 65° C. for 40 minutes. To the reaction mixture were added 12 μl of a 10-fold diluted T4 ligase buffer (pH 7.6) comprising 660 mM Tris, 66 mM MgCl$_2$, and 100 mM dithiothreitol, 3 μl of 100 mM ATP and 350 units of T4 ligase (product of Takara shuzo Co.), and the mixture was allowed to stand at 15° C. for 16 hours. The resulting reaction mixture was used for transformation of HB101 strain (ATCC33694) which is derived from *Escherichia coli* K12 and deficient in proA gene (Maniatis, et al., Molecular Cloning, A Laboratory Manual, 1982, p.504). The transformation was effected according to the method described in Molecular Cloning, A Laboratory Manual, 1982, pp.250–251. As the selection medium, a Davis minimum agar medium [a medium prepared by dissolving 2 g of glucose, 1 g of (NH$_4$)$_2$SO$_4$, 7 g of K$_2$HPO$_4$, 2 g of KH$_2$PO$_4$, 0.1 g of MgSO$_4$.7H$_2$O, 0.5 g of trisodium citrate, 4 mg of thiamine hydrochloride and 16 g of agar in an adequate amount of water, and further adding water until the total volume was one liter containing 20 μg/ml tetracycline and adjusted to pH7.2 was used. The plasmid DNA was isolated from the cultured cells of the transformants, according to the method described by Maniatis, et al. (Molecular Cloning, A Laboratory Manual, 1982, pp.86–96). The digestion by various restriction enzymes and analysis by agarose gel electrophoresis indicate that the plasmid named pPRO-1 which was isolated from the desired transformant selected from among the transformants, has a structure wherein a PstI DNA fragment of 3.0 kb having the same structure as the proAB operon reported by Deutche, et al. (Nucleic Acids Research, 12, 6337, 1984) was inserted in pBR322 at its unique PstI cleavage site. pPRO-1 was used to again transform the HB101 strain. As the selection medium, L medium (a culture medium prepared by dissolving 10 g of bactotrypton, 5 g of yeast extract, 1 g of glucose and 5 g of NaCl in an adequate amount of water, and further adding water until the total volume was one liter) containing 20 μg/ml tetracycline and adjusted to pH7.2 was used. The resulting tetracycline-resistant transformants were all proline-prototrophic, and thus it was confirmed that the proAB gene of *Escherichia coli* K12 strain was cloned. The construction process for plasmid pPRO-1 is shown in FIG. 1.

2) Preparation of mutated pPRO-1 with reduced feedback inhibition by proline

The mutated pPRO-1 with reduced feedback inhibition by proline was obtained by use of 3,4-dehydro-DL-proline (DHP), an analog of proline, in the following manner. The HB101 strain carrying plasmid pPRO-1 was treated with 400 μg/ml N-methyl-N'-nitro-N-nitrosoguanidine (NTG), and smeared on a Davis minimum agar medium containing 100 μg/ml DHP. According to the method of Smith, et al. (Journal of Bacteriology, 157, 545, 1984), with respect to the DHP-resistant strains, the activity of γ-glutamylkinase which is encoded by proB gene and subject to feedback inhibition by proline was measured. As the result, the inhibition by proline against the enzyme, had been reduced by approximately the one-hundredth in one of the DHP resistant strains, named DHP1. The plasmid which was isolated from the DHP1 strain in the manner as mentioned above and named pPRO-11, was used to retransform the HB101 strain. The obtained tracycline-resistant transformants were all growable in a medium containing 100 μg/ml DHP. In this manner, a plasmid which contained a mutated γ-glutamylkinase encoding gene with reduced feedback inhibition by proline was obtained.

EXAMPLE 2

According to the method of Ruffo, et al. (Biochemical Journal, 85, 588, 1962), 4-hydroxy-2-oxoglutaric acid was prepared. That is, 1.32 g of oxaloacetic acid and 1.14 g of sodium glyoxylate were dissolved in an adequate amount of distilled water, and the pH of the solution was adjusted to 7.4 with sodium hydroxide. A distilled water was further added until the total volume of the solution was 50 ml. The solution was warmed at 40° C. for 3 hours, and adjusted to pH 3 with hydrogen chloride. The solution was allowed to stand at room temperature for 30 minutes, and then the reaction solution was neutralized with sodium hydroxide. As a result of an assay using glutamate dehydrogenase (Methods of Enzymatic Analysis, edited by Bergmeyer, 2nd edition, Vol. 1, p.461, 1974), 0.18 mole/l of DL-4-hydroxy-2-oxoglutaric acid was produced in the reaction solution.

L medium (3 ml) was poured into a test tube, and sterilized. *Escherichia coli* ATCC33625 and *Escherichia coli* K83 were inoculated into the L medium, and cultured with shaking at 30° C. for 16 hours. The cells collected by centrifuging the culture, were sterilized and washed with a distilled water, suspended in 10 ml of a sterilized A medium [a medium prepared by dissolving 30 g of glucose, 1 g of $KH_2PO_4$, 10 g of $(NH_4)_2SO_4$, 1 g of $MgSO_4.7H_2O$, 2 mg of $FeSO_4.7H_2O$, 2 mg of $MnSO_4.7H_2O$, 30 g of $CaCO_3$ and 10 mg of thiamine hydrochloride in 1 liter of a distilled water, and adjusted to pH 7.4], and cultured with shaking in a test tube at 30° C. After 8 hours from the start of culturing, the above mentioned reaction solution containing DL-4-hydroxy-2-oxoglutaric acid (HOG) was added thereto in a concentration of 10 mM, and culturing was continued for an additional 60 hours. The amounts of trans-4-hydroxy-L-proline and cis-4-hydroxy-L-proline in the culture, determined by HPLC, are listed in Table 1.

TABLE 1

| Strain | Amount of trans-4-hydroxy-L-proline produced (mM) | | Amount of cis-4-hydroxy-L-proline produced (mM) | |
|---|---|---|---|---|
| | HOG added | no HOG added | HOG added | no HOG added |
| K83 | 0.10 | 0 | 0.11 | 0 |
| ATCC33625 | T | 0 | T | 0 |

T: a trace of amount

EXAMPLE 3

In the same manner as in Example 2, the ATCC33625 and K83 strains were cultured in A medium. After 8 hours from the start of culturing, 10 mM of HOG, 20 mM of aspartic acid (ASP) or asparagine (ASN), or 50 mM each of pyruvic acid (PYR) and glyoxylic acid (GOX) were added as indicated in Table 2, and culturing was continued for an additional 60 hours. The amounts of trans-4-hydroxy-L-proline and cis-4-hydroxy-L-proline in the culture, determined by HPLC, are given in Table 2.

TABLE 2

| Strain | Additive | Trans-4-hydroxy-L-proline (mM) | Cis-4-hydroxy-L-proline (mM) |
|---|---|---|---|
| K83 | none | 0 | 0 |
| | HOG | 0.12 | 0.12 |
| | HOG, ASP | 0.20 | 0.21 |
| | HOG, ASN | 0.21 | 0.20 |

TABLE 2-continued

| Strain | Additive | Trans-4-hydroxy-L-proline (mM) | Cis-4-hydroxy-L-proline (mM) |
|---|---|---|---|
| MM294 | PYR, GOX | 0.03 | 0.03 |
| | HOG | T | T |
| | HOG, ASP | 0.02 | 0.02 |

EXAMPLE 3

One hundred milliliters of L medium was placed in an Erlenmeyer flask, and sterilized. K83 strain was inoculated therein and cultured with shaking at 30° C. for 16 hours. The cells collected by centrifuging the culture were sterilized and washed with a distilled water. The cells were then suspended in 10 ml of a sterilized A medium, and 4-hydroxy-2-oxoglutaric acid was added thereto in a concentration of 50 mM. The reaction was carried out at 30° C. for 3 days. The amounts of trans-4-hydroxy-L-proline and cis-4-hydroxy-L-proline in the reaction mixture were 5.5 mM and 5.5 mM, respectively.

Industrial Applicability

According to the present invention, 4-hydroxy-L-proline is efficiently produced by subjecting 4-hydroxy-2-oxoglutaric acid to the action of the enzyme source which is capable of biosynthesizing 4-hydroxy-L-proline from 4-hydroxy-2-oxoglutaric acid.

We claim:

1. A process for producing 4-hydroxy-L-proline which comprises converting 4-hydroxy-2-oxoglutaric acid into 4-hydroxy-L-proline in an aqueous medium in the presence of an amino group donor and an enzyme source capable of converting 4-hydroxy-2-oxoglutaric acid to 4-hydroxy-L-proline, selected from the group consisting of a culture, cells and processed cells of a microorganism of *Escherichia coli*.

2. The process according to claim 1, wherein said conversion reaction is carried out in the presence of 4-hydroxy-2-oxoglutaric acid during the culturing of said microorganism.

3. The process according to claim 1, wherein said conversion reaction is carried out in the presence of aspartic acid or asparagine.

* * * * *